(12) United States Patent  
Daniel et al.

(10) Patent No.: US 7,448,287 B2
(45) Date of Patent: Nov. 11, 2008

(54) PIPETTE WITH AGITATION FEATURE

(75) Inventors: Jürgen H. Daniel, San Francisco, CA (US); Meng H. Lean, Santa Clara, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 0 days.

(21) Appl. No.: 11/537,700

(22) Filed: Oct. 2, 2006

(65) Prior Publication Data

US 2008/0078257 A1  Apr. 3, 2008

(51) Int. Cl.
*G01N 1/00* (2006.01)
(52) U.S. Cl. .................................... 73/864.11
(58) Field of Classification Search ............ None
See application file for complete search history.

(56) References Cited

U.S. PATENT DOCUMENTS 6,164,144 A * 12/2000 Berg ..................... 73/863.21
7,040,893 B2 * 5/2006 Fischer ..................... 433/80
2004/0251135 A1  12/2004 Lean et al.
2004/0251136 A1  12/2004 Lean et al.
2004/0251139 A1  12/2004 Lean et al.
2005/0123930 A1  6/2005 Lean et al.
2005/0123992 A1  6/2005 Volkel et al.
2005/0247564 A1  11/2005 Volkel et al.
2005/0247565 A1  11/2005 Hsieh et al.
2006/0038120 A1  2/2006 Lean et al.
2007/0166660 A1 * 7/2007 Peuker et al. ............. 433/89

* cited by examiner

*Primary Examiner*—Robert R Raevis
(74) *Attorney, Agent, or Firm*—Fay Sharpe LLP

(57) ABSTRACT

A system and method extracts/deposits fluid and includes a pipette having a pipette body portion and a pipette tip. A stirring/agitation mechanism including a fiber or a rod extends through the interior of the pipette tip, wherein a fiber end or rod end of the fiber or rod, extends out of a narrowed end of the pipette tip, and the fiber end or rod end is configured to stir or agitate the fluid.

21 Claims, 13 Drawing Sheets

PIPETTE WITH AGITATION FEATURE

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Contract No. W911NF-05-C-0075 awarded by the U.S. Army.

BACKGROUND

The present application relates to the field of extracting/depositing of fluid, and more particularly, to stirring/agitating of fluid to increase extraction of particles within the fluid and/or mixing of different fluids.

Extracting a sample fluid from a collection chamber of a fluidic system can be challenging, particularly when the collection chamber contains small amounts of fluid, such as in the range of approximately 1.5 milliliters to 10 microliters.

To extract fluid from a fluidic system such as a micro-well or micro-channel, a pipette is often used. If the fluid contains particles, such as organic or inorganic materials or biomaterials, the particles may become adhered to the container bottom or the container sidewalls. In these situations, the extracted fluid sample will have a reduced concentration of particles, this loss may compromise tests performed on the extracted fluid sample, comprising the limits of detection and producing increased false positives and ambiguity when the sample is analyzed. To increase the amount of particles extracted by a pipette, it is desirable to stir the fluid during the extraction process in order to disperse the particles from the channel walls and bottom, thereby increasing the likelihood that more particles are collected during the process. Adhesion of the particles may occur due to adhesive forces such as electrostatic or Van der Waals attractive forces.

Another use of fluidic systems is for mixing together two distinct fluids, for example, to obtain a chemical reaction, heat transfer, etc. Often the two fluids do not mix rapidly simply by bringing them together (i.e., only slow mixing occurs due to diffusion), resulting in a slow and incomplete mixing of the fluids. This result may affect the outcome of the process which may have been undertaken for commercial and/or experimental reasons. In each of the above situations and others, an active mixing of fluids may by desirable. Mixing may be useful when the fluid from the pipette is dispensed into a vial or a fluidic reservoir with another fluid. The mixing fluids may be used for an analysis or for an experiment.

One proposal for the agitation or stirring of fluids is by the use of a bead stirrer or external ultrasonic agitation. An alternative form of agitation is by fluid-flow induced agitation accomplished by pulsing the pipette, i.e., back and forth pumping of the liquid by application of an external pressure source. Examples of such ultrasonic and fluid-flow agitation are set forth in patents and applications cited within the Incorporation by Reference section of this document.

INCORPORATION BY REFERENCE

U.S. Patent Application Publication No. US2004/0251135A1 (U.S. Ser. No. 10/459,799, Filed Jun. 12, 2003), published on Dec. 16, 2004, by Meng H. Lean et al., and entitled, "Distributed Multi-Segmented Reconfigurable Traveling Wave Grids for Separation of Proteins in Gel Electrophoresis"; U.S. Patent Application Publication No. US2005/0247564A1 (U.S. Ser. No. 10/838,570, Filed May 4, 2004), published on Nov. 10, 2005, by Armin R. Volkel et al., and entitled, "Continuous Flow Particle Concentrator"; U.S. Patent Publication No. US2005/0247565A1 (U.S. Ser. No. 10/838,937; Filed May 4, 2004), published on Nov. 10, 2005, by Hsieh et al., and entitled, "Portable Bioagent Concentrator"; U.S. Patent Application Publication No. US2004/0251139A1 (U.S. Ser. No. 10/460,137, Filed Jun. 12, 2003), published on Dec. 16, 2004, by Meng H. Lean et al., and entitled, "Traveling Wave Algorithms to Focus and Concentrate Proteins in Gel Electrophoresis"; U.S. Patent Application Publication No. US2005/0123930A1 (U.S. Ser. No. 10/727,301, Filed Dec. 3, 2003), published on Jun. 9, 2005, by Meng H. Lean et al., and entitled, "Traveling Wave Grids and Algorithms for Biomolecule Separation, Transport and Focusing"; U.S. Patent Application Publication No. US2005/0123992A1 (U.S. Ser. No. 10/727,289, Filed Dec. 3, 2003), published on Jun. 9, 2005, by Volkel et al., and entitled, "Concentration and Focusing of Bio-Agents and Micron-Sized Particles Using Traveling Wave Grids"; U.S. Patent Application Publication No. US2004/0251136A1 (U.S. Ser. No. 10/460,724, Filed Jun. 12, 2003), published on Dec. 16, 2004, by Meng H. Lean et al., and entitled, "Isoelectric Focusing (IEF) of Proteins With Sequential and Oppositely Directed Traveling Waves in Gel Electrophoresis"; and U.S. Patent Application Publication No. US2006/0038120A1 (U.S. Ser. No. 10/921,556, Filed Aug. 19, 2004), published Feb. 23, 2006, by Meng H. Lean et al., entitled "Sample Manipulator", U.S. Application No. 11/468,523, filed Aug. 30, 2006, entitled, "Particle Extraction Methods And Systems For A Particle Concentrator", by Meng H. Lean et al. ; and U.S. Application Publication No. 20080081004A1, (U.S. Ser. No. 11/537,679, filed Oct. 2, 2006, entitled, "Fluid Stirring Mechanism", by Jürgen H. Daniel et al., each hereby incorporated herein by reference in their entireties.

BRIEF DESCRIPTION

A system and method extracts/deposits fluid and includes a pipette having a pipette body portion and a pipette tip. A stirring/agitation mechanism including a fiber or a rod extends through the interior of the pipette tip, wherein a fiber end or rod end of the fiber or rod, extends out of a narrowed end of the pipette tip, and the fiber end or rod end is configured to stir or agitate the fluid.

BRIEF DESCRIPTION OF THE DRAWINGS

The present subject matter may take form in various components and arrangements of components, and in various steps and arrangements of steps. The drawings are only for purposes of illustrating preferred embodiments and are not to be construed as limiting the subject matter.

DETAILED DESCRIPTION

Figure 1A:
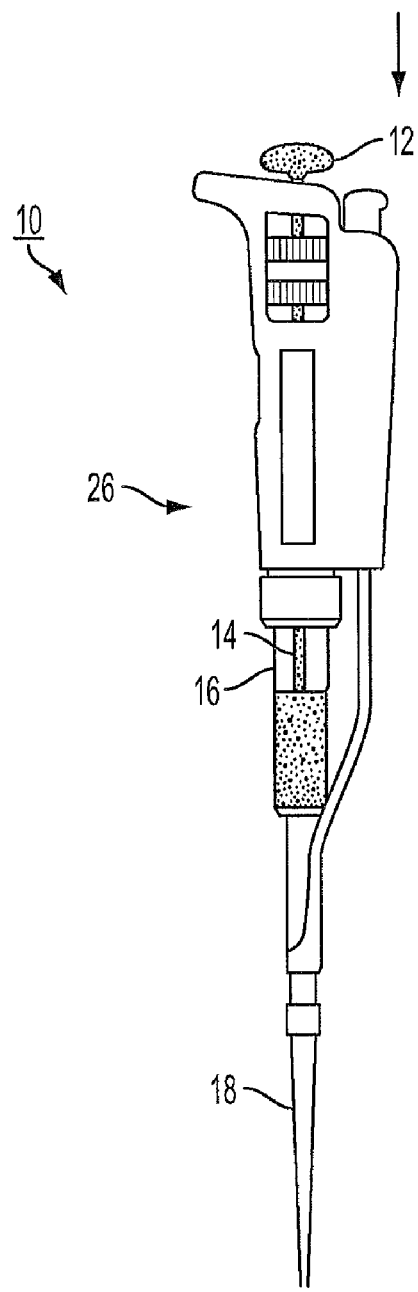
FIGS. 1A-1B are a schematic drawings of an existing pipette system.
Figure 1B:
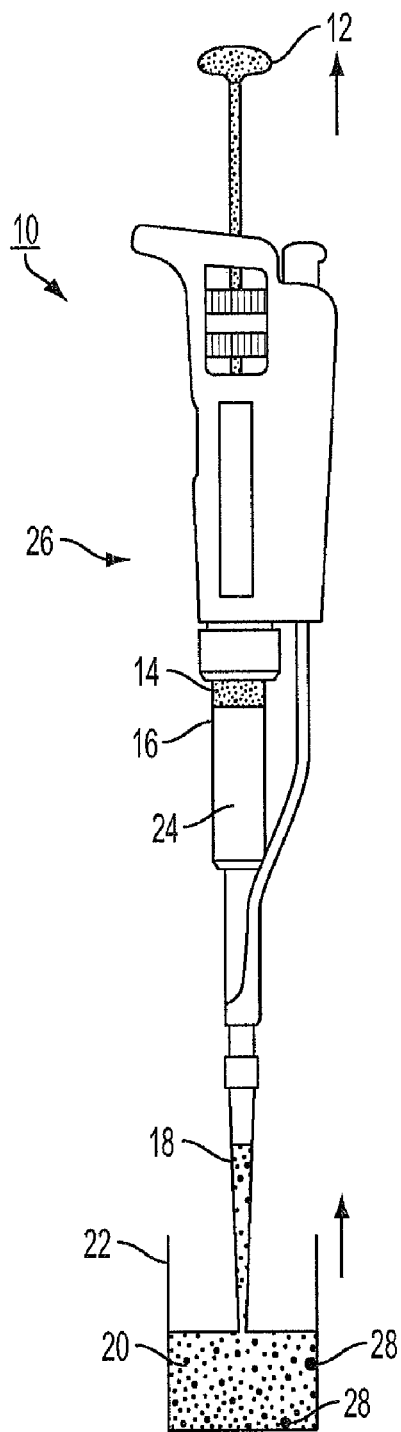

FIGS. 1A-1B depict a known pipette device 10, in purged and aspirated position, respectively. A pipette works by creating a vacuum above a liquid holding chamber to draw liquid and by releasing the vacuum or applying pressure to dispense liquid. Pipettes cover a wide range of volumes, ranging from microliters to milliliters. Pipettes that dispense between 1 and 1000 microliters are termed micropipettes, while macro-pipettes dispense a greater volume of liquid, typically up to 10 mL and in some cases up to 50 mL. Even greater volumes are covered by larger pipettes such as for example aquatic pipettes.

Pipette 10 includes plunger 12 in operative association with piston 14, maintained in shaft 16. The shaft 16 leads down through the device to pipette tip 18, which commonly is the portion of the device which holds an extracted fluid sample 20, originally held in container 22. During extraction, air cushion 24 is maintained between fluid sample 20 and shaft portion 14. Pipette 10 also includes a chassis or pipette body portion 26 having an interior area which holds at least portions of plunger 12, piston 14 and shaft 16. Pipette tip 18 may be disposable, and therefore can be connected/disconnected from chassis 26 at chassis end 26a.

In one operation, plunger 12 is depressed, as depicted in FIG. 1A to purge any air or other fluid. Normal operation consists of depressing plunger 12 to a first stop while the pipette is held in the air. Pipette tip 18 is then submerged into liquid 20, and plunger 12 is released in a slow and even manner. This draws liquid 20 up into tip 18. Pipette 10 is then moved to a desired dispensing location. The plunger 12 is then depressed to a first stop, and then to a second stop or blow-out position. This action evacuates tip 18, dispensing or placing liquid 20 at a desired location. In an adjustable pipette, the volume of liquid contained in the tip 18 is variable, i.e., it can be metered/changed via a dial or other mechanism, depending on the pipette type.

With continuing attention to FIGS. 1A-1B, at least some of particles 28, which may be organic, inorganic materials or biomaterials such as spores or bacteria, etc., are shown adhered to the sidewalls and bottom of container 22. As previously mentioned, adhesion may occur due to electrostatic attraction, Van der Waals bonding, or other adhesion effects. Thus, when pipette 10 is operated to obtain sample fluid 20, adhered particles 28 are not extracted, resulting in a diluted sample being drawn up into tip 18. This, again, is undesirable and therefore a manner to increase the percentage of particles drawn up into tip 18 is considered useful.

Figure 2:
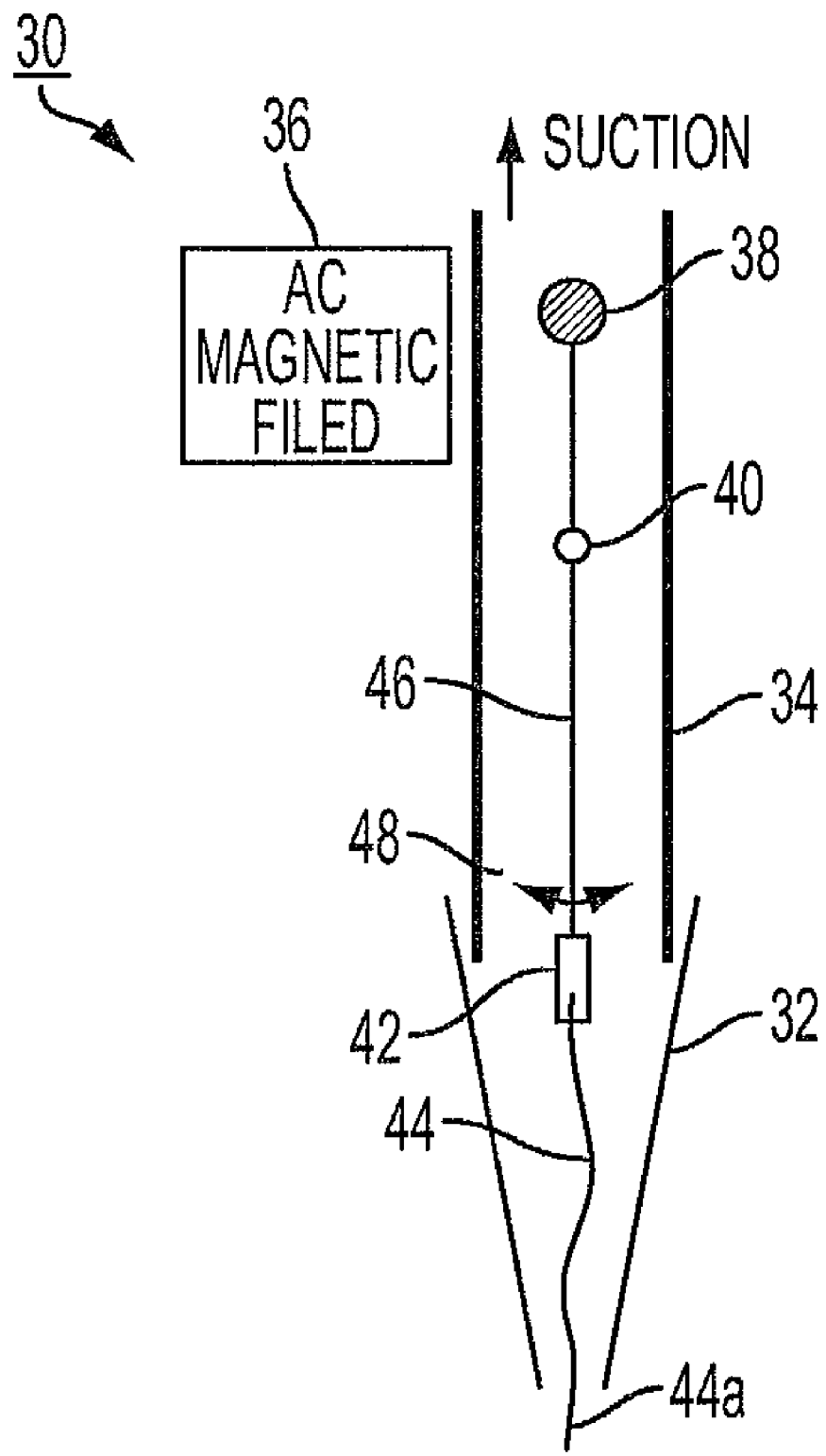
FIG. 2 is a cross-section schematic of a pipette with a vibrating fiber in accordance with the concepts of the present application.

Turning to FIG. 2, a first embodiment for a pipette 30 designed to increase particle extraction is disclosed. It is noted the upper part of the pipette which provides the metering and aspiration/dispensing mechanisms are not shown in FIG. 2, with attention more specifically directed toward the lower portion of the pipette. Thus, FIG. 2 depicts pipette tip 32 and lower pipette portion 34. In this embodiment pipette tip 32 may be disposable, and therefore the interconnection between pipette tip 32 and lower pipette portion 34 is designed to allow pipette tip 32 to be removed, and a new pipette tip attached. Such attachment/disposal is known in the art.

Lower pipette portion 34 further includes a generator 36 such as an AC magnetic field generator, actuation point 38, pivot point (or fulcrum) 40, fiber connector 42, and disposable fiber 44, interconnected to each other by extending member 46 within lower pipette section 34. Extending member 46 may be an appropriate flexible, rigid or semi-rigid tube, fiber, rod or other element which permits the desired connections. The generator 36 generates a force or a field (such as a magnetic field) which is directly or indirectly coupled to the actuation point 38. Generator 36 may be an AC magnetic field generator which couples the magnetic field to a magnet mounted at the actuation point 38 (i.e., an example of indirect coupling) or it may be an electric motor which is mechanically linked to the actuation point. The generator 36 may also generate an actuation force by other mechanisms such as piezo vibration, electrostriction, electroactive polymer actuation, thermal actuation, pneumatic or fluidic actuation, etc. In at least some embodiments, the generator is capable of moving the actuation point at different frequencies. In this embodiment, the generator is placed external to the interior of lower pipette section 34. It is to be appreciated, however, in other embodiments the generator may be located at other positions, for example it may be integrated in the upper part of the pipette and the generator may be directly or indirectly coupled to the actuation point 38. Pivot 40 may be used to hold the arrangement within the pipette. For example, it may be loosely held within the interior. Examples of how the pivot (or suspension element) may be held are discussed below.

Figure 3A:
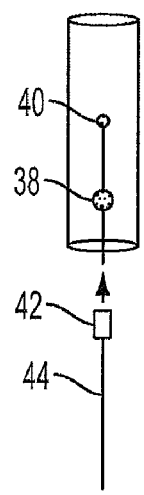
FIGS. 3A-3C set forth steps for mounting a fiber-end pipette tip in accordance with the concepts of FIG. 2.
Figure 3B:
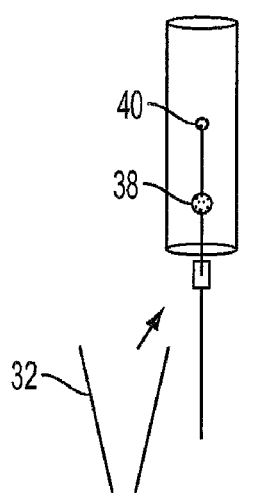
Figure 3C:
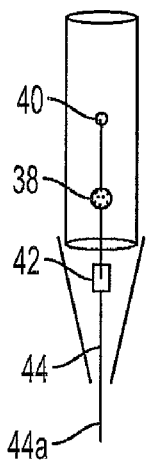

Turning to FIGS. 3A-3C and with continuing attention to FIG. 2, the steps for mounting disposable fiber 44 and pipette tip 32 to lower pipette section 34 is illustrated. More particularly, fiber 44 is interconnected with lower portion of extending member 46, wherein in this embodiment fiber 44 has a fiber connector 42 configured in order to make attachment to extending element 46. Particularly, the connection may be through a press-fit, clip-on, stick-on mechanism or other known attachment arrangement. Additionally, in alternative embodiments, extending element 46 may contain the clip-on, press-fit or other mechanism to which the end of fiber 44 is attached. Once connection is made between fiber 44 and extending element 46, pipette tip 32 is concentrically attached to lower pipette section 34 by known techniques, such as a press-fit attachment. In this way, fiber 44 is located within pipette tip 32, with its fiber end 44a extending past the end of pipette tip 32. Since the pipette tip is shaped as a funnel, with a decreasing diameter, insertion of the fiber is a self-guided process. It is to be appreciated that a difference between FIG. 2 and FIGS. 3A-3C is the positioning of actuation point 38 and pivot 40. Repositioning of these components is intended to show that alternative arrangements of the components are possible.

Figure 4A:
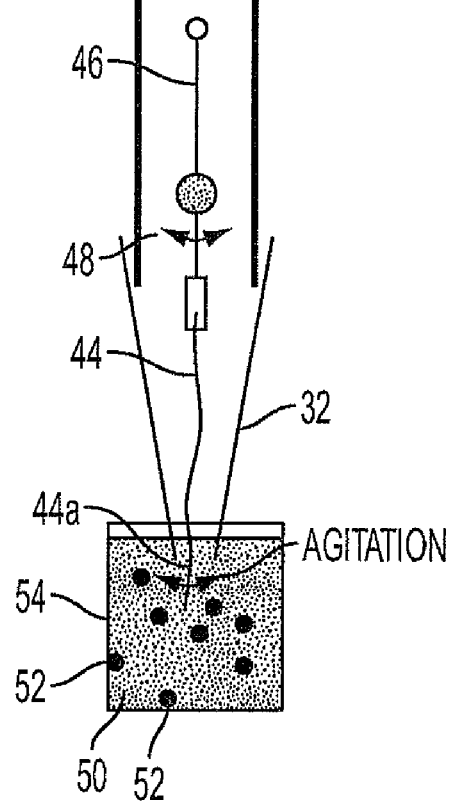
FIGS. 4A-4B illustrate a fluid extraction process incorporating the concepts of the present application.
Figure 4B:
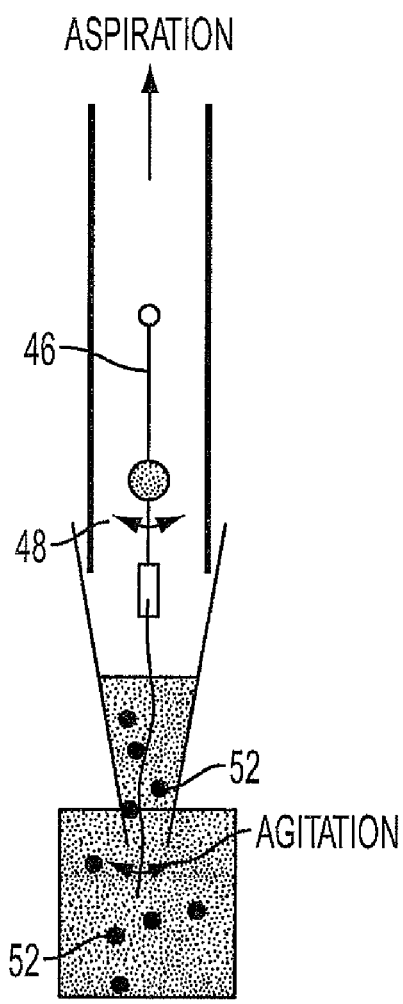
Figure 5:
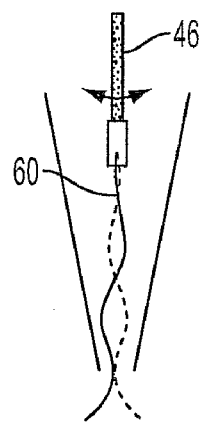
FIG. 5 depicts a design for the pipette tip with agitation mechanism in accordance with the present application.

With continued attention to FIG. 2 and additional attention to FIGS. 4A and 4B, stirring/agitation operation by fiber 44 is accomplished by selective activation of generator 36. More particularly, when generator 36 is activated, actuation point 38 is alternatingly attracted and repelled causing movement as illustrated by arrow 48 (see FIG. 2). Such activation causes the fiber to oscillate whereby fiber tip 44a moves back and forth within a sample 50 having fluid particles 52, some of which have adhered to side walls or bottom of sample container 54, where some of those at the bottom, may have settled at the bottom due to gravitation forces. Thus in FIG. 4A, the fluid with particles is agitated in order to disperse the particles into a suspended state within fluid 50. Although the fiber movement is shown as a back and forth motion, it can be more complex and be for example a circular motion if the actuation force deflects the actuation point in a circular pattern. Apart from the above mentioned removal of adhered particles, generally, the stirring mechanism is intended to render non-uniform or inhomogeneous fluids more uniform or homogeneous. These can be fluids containing particles (such as bacteria or spores, etc.), they can be two or more fluids which are not well mixed, fluids with a temperature gradient or with a non-uniform temperature distribution or otherwise non-uniform fluids. A particular use for the rendering of non-uniform or inhomogeneous fluids more uniform or homogeneous includes, but is not limited to, biological and/or chemical analysis.

In a first embodiment, as shown in FIG. 4B, agitation continues during the extraction process, i.e., as fluid 50 is moved into pipette tip 32. As can be seen by this figure, particles 52, which were adhered to the sidewalls or bottom of the container are now brought up into pipette tip 32. Thus, the agitation created by fiber 44 increases the percentage of particles which are extracted.

Figure 6:
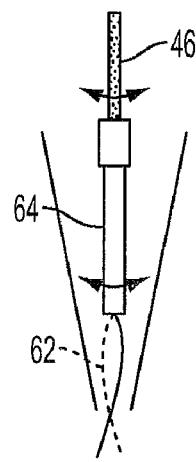
FIG. 6 depicts an alternative design for the pipette tip with agitation mechanism.
Figure 7:
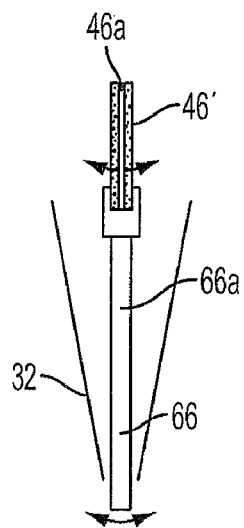
FIG. 7 depicts still a further embodiment of a pipette tip with agitation mechanism.

FIGS. 5, 6, 7 and 8A-8B illustrate alternative embodiments for the stirring/agitation configuration. For example, in FIG. 5, fiber 60 is similar to fiber 44, and is provided to show the oscillation of a long fiber extension within pipette tip 32. FIG. 6 illustrates the oscillations for a flexible fiber 62, which is shorter and attached to a rigid element 64. It might be expected that the force generated by a short fiber 62 could be greater than the force generated by a longer fiber, as less energy is lost in its transfer to the end of the fiber. In FIG. 7, the "fiber" is configured as a thin, rigid capillary, tube or rod (for example, glass, stainless steel, polymer or other appropriate material) 66. Of course while the capillary, tube or rod 66 of FIG. 7 is described as rigid, it may flex to some degree, particularly when it is a polymer tubing or a thin capillary. In this design, motion is again in the same lateral direction. However, it is understood the motions for the concepts of this application can be also out of plane or circular around the axis of the pipette, as with the other designs.

In the embodiment of FIG. 7, the fluid is aspired through center 66a of rod 66, and pipette tip 32 only acts as mechanical support or as an alignment structure to guide the pipette into a micro-channel or other fluid container. Pipette tip 32 also protects rod 66 from mechanical damage. With further attention to extraction of the fluid through the interior or center 66a of rod 66, extending element 46' is designed with an interior 46a through which a vacuum is provided to move the fluid into rod 66.

Figure 8A:
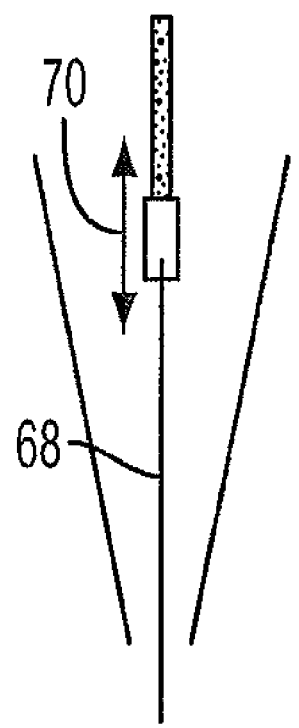
FIGS. 8A-8B show still a further tip where agitation mechanism concept is disclosed.
Figure 8B:
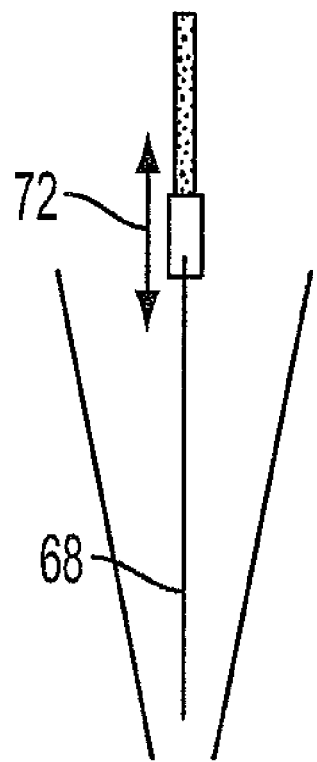

Turning to FIGS. 8A and 8B, an alternative concept to stirring/agitation is illustrated in which fiber 68 is extended into (FIG. 8A) and extracted from (FIG. 8B), a fluid as shown by arrows 70 and 72, respectively. This up-and-down actuation scheme may be used to stir the liquid. In this case the actuation point provides an oscillation of the extending member which is essentially parallel to the longitudinal axis of the pipette. The stirring is particularly effective in this case if the end of the fiber 68 is bent, curved, spiraled, of if it has a paddle-like extension. The up-and down actuation scheme shown in FIG. 8A and FIG. 8B may also be useful in the case of the lateral actuation schemes described before. In this case the up and down actuation of the fiber may be rather understood like the actuation of a ball-point pen. In one state the fiber is extended in order to agitate the external fluid, in the second state the fiber is retracted into the pipette tip. In this retracted state the fiber may still be able to vibrate. For example, when dispensing the collected sample from the pipette tip into another reservoir, the vibration may help to prevent adhesion of particles to the inner walls of the pipette tip and to the surface of the fiber. For each of the above described designs, the fibers may also be electrically conducting in order to attract charged ones of the particles in the fluid or in order to prevent adhesion due to tribocharging.

Figure 9:
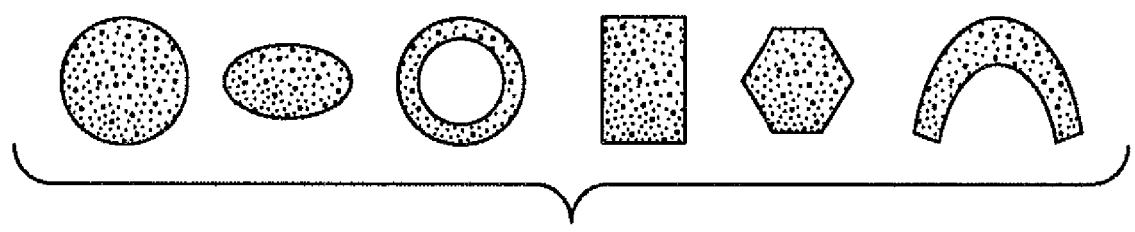
FIG. 9 illustrates potential cross sections for the fiber or rod used in the concepts of the pipette tip and agitation mechanism.
Figure 10:
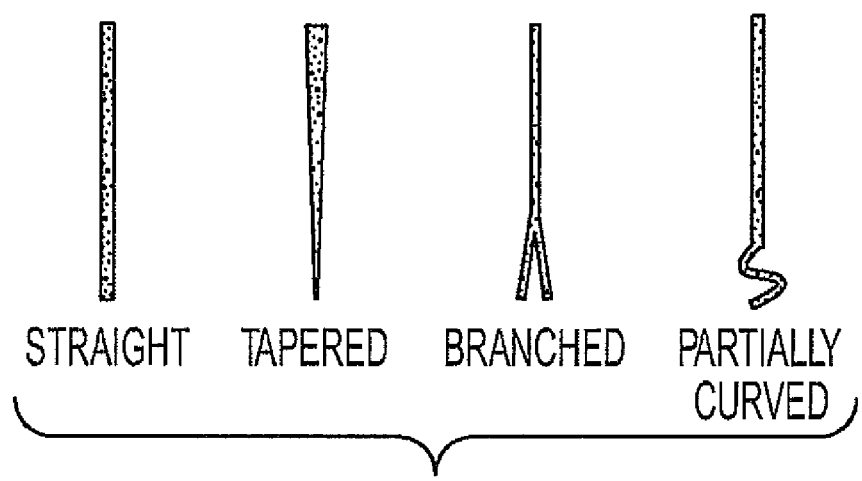
FIG. 10 illustrates side views of the fiber or rod used in agitation mechanism of the present application.

The fiber and/or rods described in the foregoing embodiments have been generally represented as substantially uniform, circular fibers or rods, however, it is to be appreciated they may be provided in a variety of designs. For example, as illustrated in FIG. 9, the fibers may be configured in multiple cross sections, and as shown in FIG. 10, the fibers do not need to be simply a straight, but may have tapered, branched or partially curved portions. It is to be understood, the embodiments shown in FIGS. 9 and 10 are simply representative, and further fiber or rod configurations may be used within the concepts of the present application.

The fiber/rod may be made from a material such as a metal, a polymer, glass, ceramic and other materials, and may also consist of two (or multiple) sections made of different materials, for example to achieve different levels of stiffness. In one example, the stirring fiber/rod may consist on one end of a rather rigid metal (e.g., steel) tube/rod which connects to the actuation mechanism and at the other end of a rather flexible polymer (e.g., nylon) fiber. The fiber, particularly in the case of polymer fiber/rod, may be fabricated by known methods such as extrusion, molding, laser-cutting, laser-welding, embossing, stamping, etc. The fiber/rod may be of a number of different sizes. However, in particular embodiments where the fluidic systems are micro-/miniature fluidic systems, the fiber/rod is in the range of approximately 25-1,000 microns in diameter, and in some other embodiments, a diameter in the range of approximately 50-500 microns, are used. It is to be understood the diameters discussed here are to the body of the fiber or rod, and that bristles, arms, etc. extending from the body may extend outside these diameters.

The aperture of the pipette tip 32 may not be just round, but it may be shaped oval, or rectangular. Such designs would allow a larger deflection of the fiber at least in one direction if a vibration node of the fiber does not coincide with the location of the aperture.

Figure 11A:
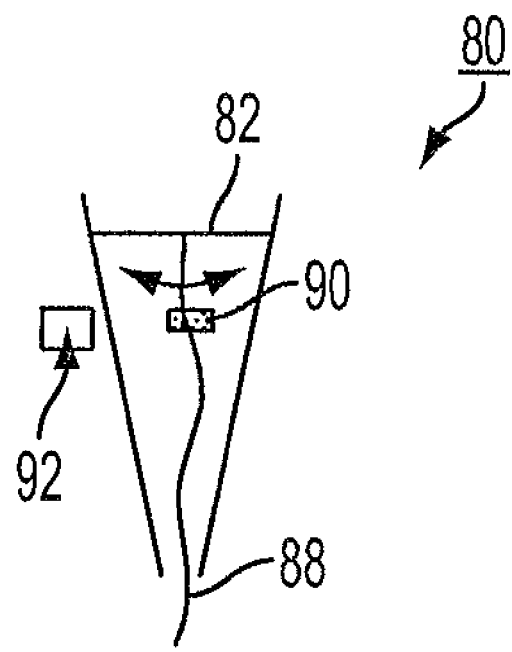
FIGS. 11A-11B set forth side and top views of a exemplary pipette tip with integrated fiber.
Figure 11B:
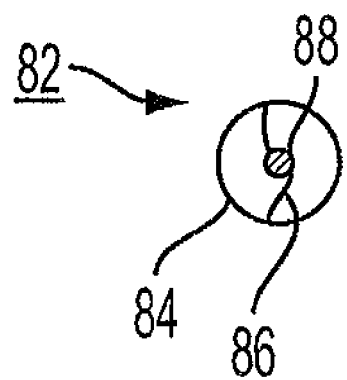

Turning to FIGS. 11A and 11B, set forth is an alternative pipette arrangement, wherein the pipette tip is configured with an integrated fiber. More particularly, FIG. 11A is a side view of pipette tip 80, which includes a fiber suspension component 82, shown in top view in FIG. 11B, and which includes frame 84 from which extensions 86 are used to hold fiber 88. Frame 84 is sized to fit within pipette tip 80 in a secure fashion, and may be glued, molded into or otherwise held by known techniques within pipette tip 80. Fiber 88 which extends down through and out of the lower opening of pipette tip 80, has an actuation point which is provided at magnet or other element 90. The magnet may be a paste magnet (e.g. magnetite particles mixed in a polymer), or other small magnet structure. Generator 92 which in this embodiment is an AC magnetic field generator 92 is selectively actuated to cause fiber 88 to vibrate as previously discussed. Fiber 88 may of course be a more rigid element such as a rod. It is to be appreciated, and similar to previous embodiments, generator 92, while shown to be exterior to the pipette tip, may be integrated within the pipette and not a separate external element. Particularly, the structure shown in this figure, as well as the previous embodiments and the following embodiments may be held within the interior of the pipette or pipette tip, such as within the interior of the chassis of FIGS. 1A-1B.

Figure 12A:
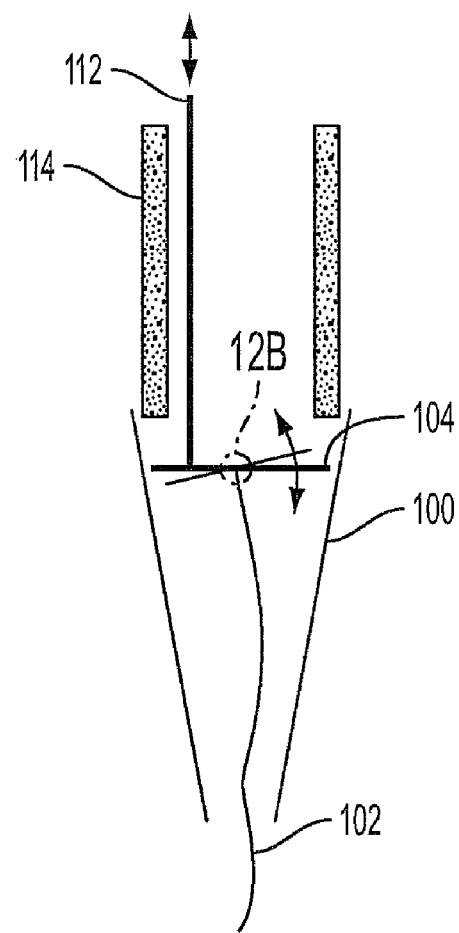
FIGS. 12A-12B illustrate schematic drawings of an alternative exemplary pipette tip with integrated fiber concepts.
Figure 12B:
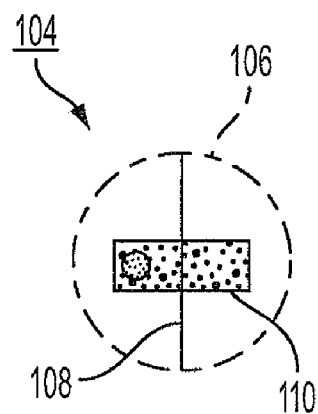

Turning to FIGS. 12A and 12B, an alternative pipette tip 100 with an integrated fiber 102 is illustrated. As shown in top view 12B, fiber suspension component 104 includes a frame 106 from which extends a cross beam 108, to which is connected a tipping mechanism 110. The suspension element is integrated within pipette tip 100 to allow fiber 102 to extend through its opening. In this arrangement, the actuation point is provided by a plunger 112 located within pipette body 114, wherein depression of plunger 112 causes movement of tipping mechanism 110, causing vibration of fiber 102. Plunger 112 may be manually activated by a button which a user may selectively depress, or the plunger may be automatically actuated by an internal motor, a piezo-actuator, an electro-strictive actuator, a magnetic actuator or other appropriate mechanism.

Figure 13:
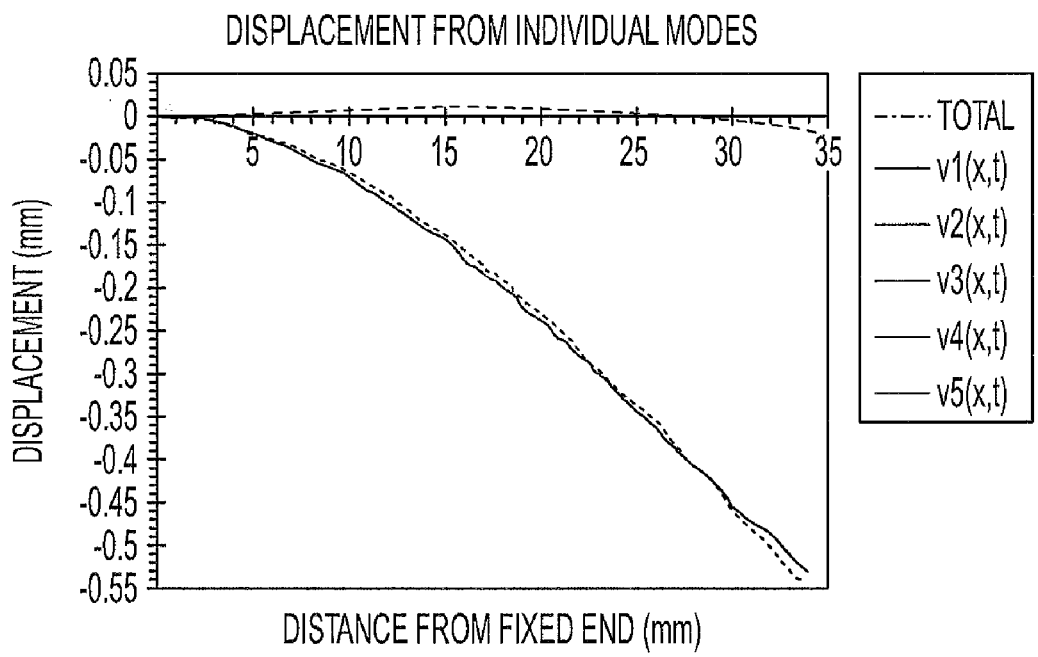
FIG. 13 provides a chart illustrating displacement of a suspended cantilever when vibrating at a first resonant mode.
Figure 14:
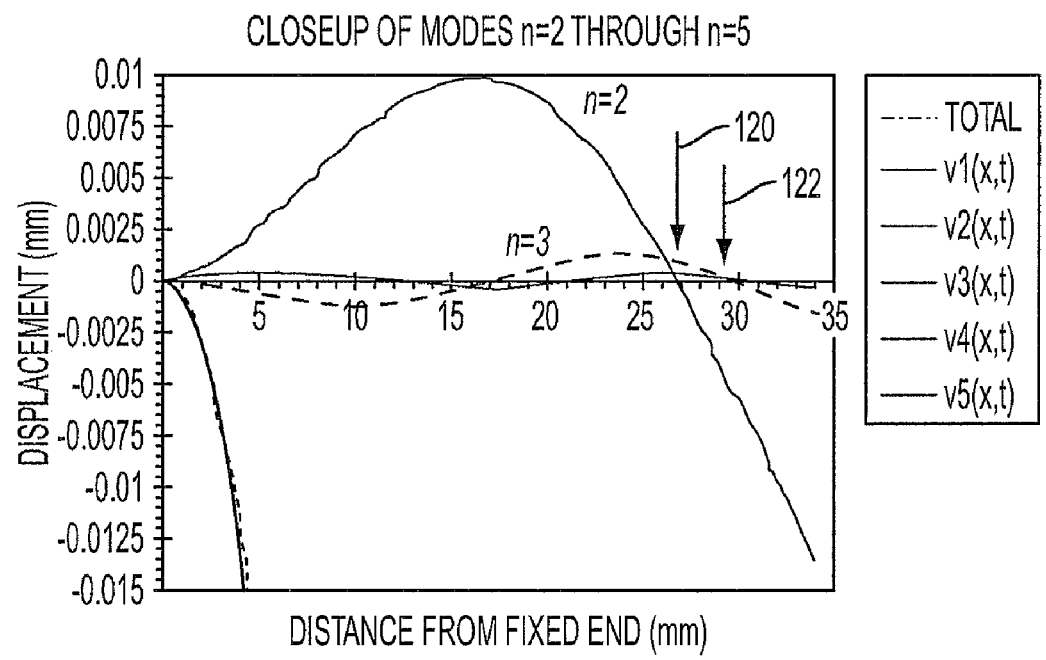
FIG. 14 shows the displacement of a suspended cantilever when vibrating at a mode2 and a mode3.

Turning to FIGS. 13 and 14, shown are displacements of a suspended cantilever (unknown dimensions) when vibrating at various resonant modes. Arrow 120 indicates the location of minimum deflection in mode2 and arrow 122 indicates the location of minimal deflection in mode3. These locations would preferably coincide with the narrow exit hole or aperture of the pipette tip. In order to find these modes, the excitation frequency may be continuously swept through a frequency range. Particularly, the generator of the embodiments described herein, including but not limited to the AC magnetic generator, may be powered to scan multiple frequencies. When using a motor as the generator for the actuation force, the frequency sweep would be achieved by periodically varying the rpm (revolutions per minute) value. It is to also be appreciated that, in finding the desired excitation frequency, the particular fluid (viscosity and particle loading) which is being extracted may have an influence in determining the resonant frequency. Particularly, the viscosity of the fluid and the amount of particles in the fluid (e.g., particle loading) will influence the resonant frequency.

Figure 15:
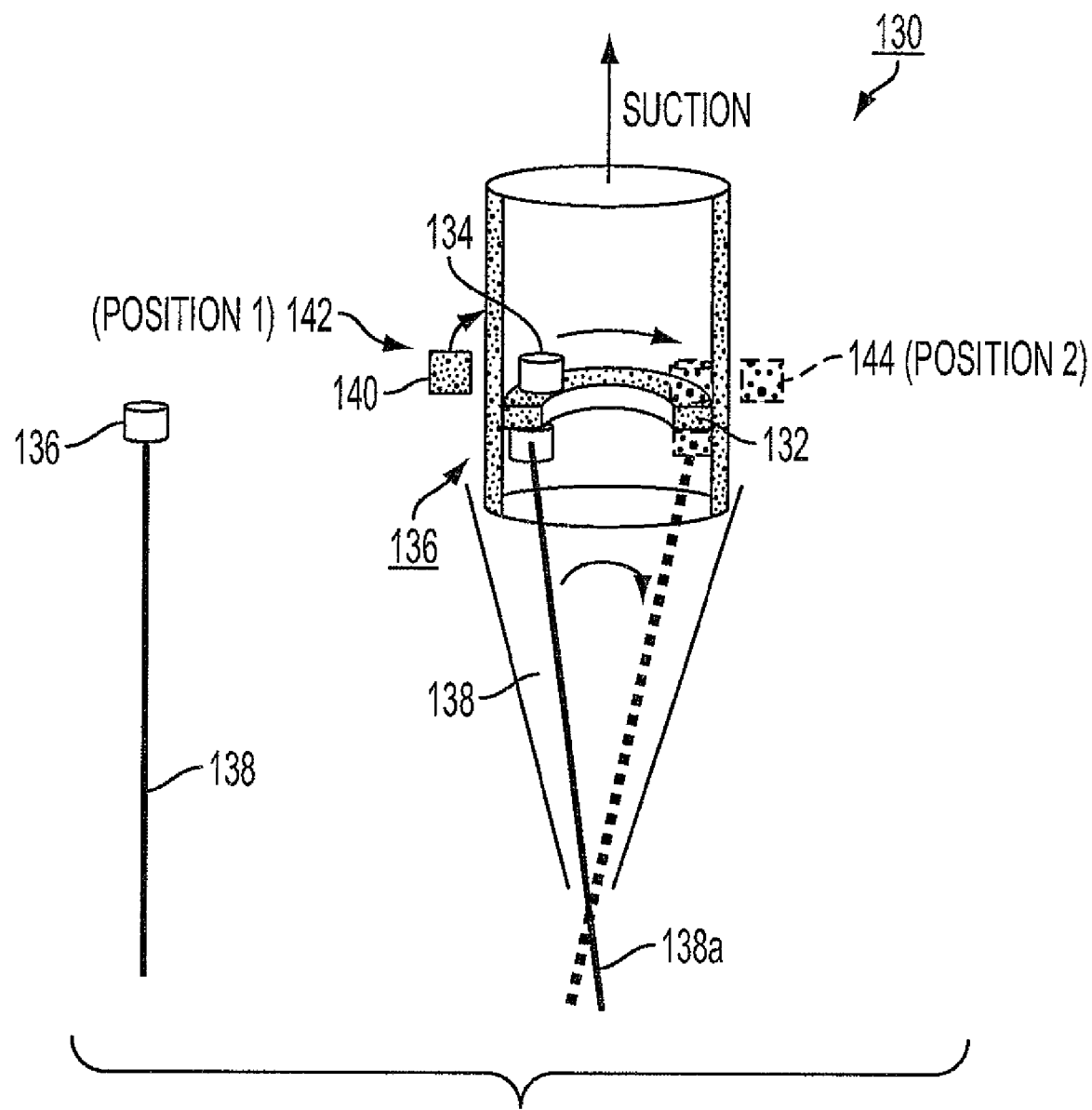
FIG. 15 is an illustration of yet another exemplary mechanism for vibrating or agitating a fiber/rod inside a pipette.
Figure 16A:
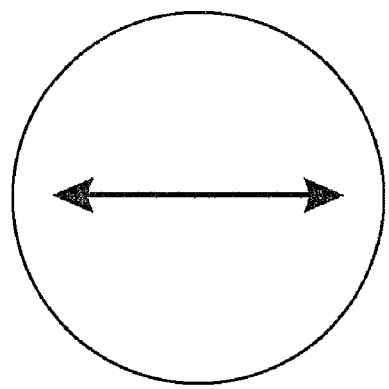
FIGS. 16A-16C are top views of linear, circular and combination actuation patterns.
Figure 16B:
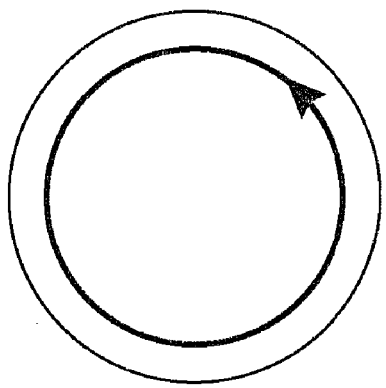
Figure 16C:
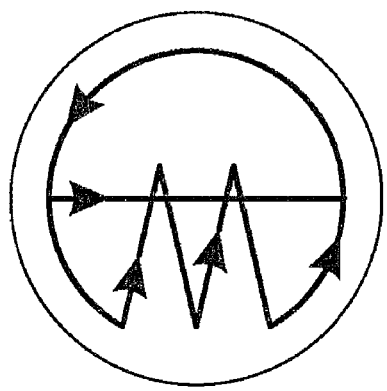
Figure 17A:
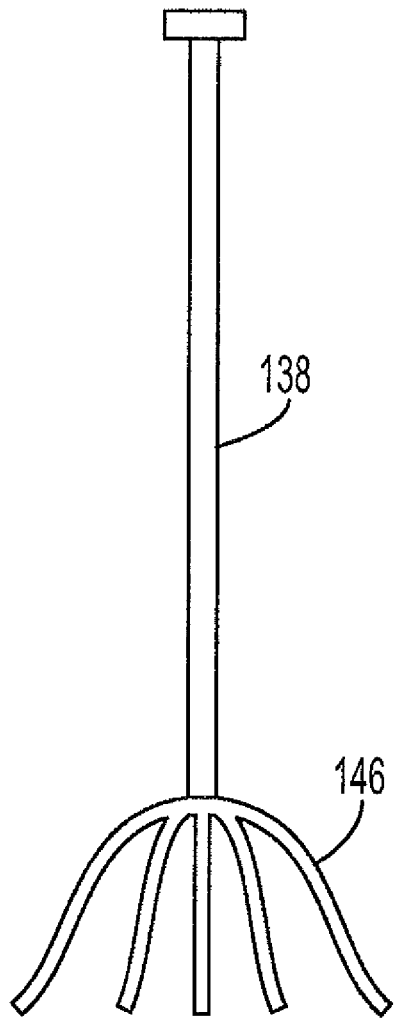
FIGS. 17A-17B illustrate embodiments of a rigid fiber or rod having a paddle and a more flexible member attached, respectively.
Figure 17B:
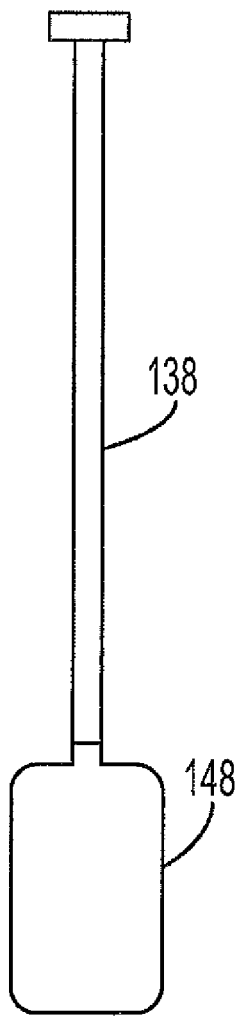

Turning to FIG. 15, set forth is another pipette 130, incorporating an exemplary embodiment for a mechanism which vibrates a fiber/rod inside the pipette tip. In this design, a spacer element 132 is provided within an interior section of pipette 130. On a first or upper surface of spacer 132 is first or upper rotating internal magnet 134, and on a second or lower surface is second or lower rotating internal magnet 136. Second or lower rotating internal magnet 136 is connected to fiber or rod 138. Magnets 134 and 136 are kept from falling away from spacer 132 by the magnetic effect of each magnet 134 and 136 on each other, through spacer 132. Also, an actuation point is provided by an external rotating magnet 140. In operation, the actuation point provided by the external rotating magnet 140 may be at a first position (position1) 142, located in operative association with first or upper rotating magnet 134. More particularly, external magnet 140 and rotary magnet 134 may be configured to either attract or repel each other. When the magnets are attractive to each other, magnet 140 is pulling magnet 134, and when they repel each other, magnet 140 pushes magnet 134. Thus, when external rotating magnet 140 is moved to a second position (position2) 144, the magnetic effects cause first or upper rotating magnet 134 to move to position2, thereby causing second or lower rotating internal magnet 136 to also move around spacer 132 to position2 144. This movement activates fiber 138, causing extending fiber end 138*a* to vibrate or oscillate. External magnet 140 may be moved in a number of fashions, including manually, by a motor, or another appropriate process. Again, while external magnet 142 is shown external to the interior of pipette 130, the pipette can be fashioned so as to be a single unit. Also, while magnet 140 is depicted, in this embodiment, as moving magnet 134, magnet 140 may be positioned to move magnet 136. A particular concept of FIG. 15 is the mode in which the fiber or rod 138 moves. The fiber or rod 138 rotates around the surface of a virtual cone. The tip of the cone (i.e., the fulcrum of the fiber or rod movement) is located at the narrow exit hole or aperture of the pipette tip. In contrast to the vibrations shown before, e.g., in FIG. 5, this stirring configuration mechanism does not require a rather flexible fiber (since the fiber/rod does not need to be driven into a bending mode). The fiber or rod 138 can be rather stiff (e.g. a thin steel tube) and therefore it may be less sensitive to viscosity changes of the fluid to be stirred. In this mechanism, there is also no resonant mode. As shown in FIG. 15, the top end of the fiber or rod 138 may be moved (forced) in a half-circle (i.e., back and forth between Position1 and Position2), a full circle (i.e., from Position2, back to Position1), or some variant thereof. Alternatively, the top end of the fiber or rod 138 may also be simply agitated back and forth in a linear motion using an actuation mechanism similar to the one shown in FIG. 2, FIGS. 3A-3C and FIG. 7. Thus, as shown in the top views of FIGS. 16A, 16B and 16C, any of a variety of actuation patterns may be used to move both flexible and rigid fibers or rods in accordance with the present concepts. It is to be appreciated, therefore, any of the number of actuation patterns may be chosen and the frequency of actuation may also be varied. The end of the rigid fiber or rod 138 may have a more flexible member attached which may act like a brush 146 or a paddle 148 as depicted in FIGS. 17A and 17B, respectively.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is;

1. A system for stirring/agitating and extracting/depositing fluid, comprising:
   a pipette including a pipette body portion and a pipette tip;
   a stirring/agitation mechanism including a fiber or rod extending through an interior of the pipette tip, wherein a fiber end or a rod end of the fiber or rod extends out of a narrowed aperture of the pipette tip, and the fiber end or rod end is configured to stir or agitate the fluid.

2. The system according to claim 1, wherein the stirring/agitation mechanism further includes:
   an extending member connected at one end to an end of the fiber or rod;
   an actuation point operatively associated with a second end of the extending member; and
   a generator placed in operative association with the actuation point, wherein operation of the generator causes movement of the actuation point, which in turn causes movement of the fiber or rod.

3. The system according to claim 2, wherein the fiber or rod is detachable from the extending member.

4. The system according to claim 1, wherein the stirring/agitiation mechanism further includes a rigid element connected between an extending member and the fiber or rod.

5. The system according to claim 1, further including the fiber or rod configured as a fiber or rod with a hollow interior for receiving the fluid.

6. The system according to claim 1, further including an actuation point configured to move the fiber or rod in a linear motion, a circular motion, or a combination of these motions, within the fluid.

7. The system according to claim 1, further including an actuation point configured to move in an up-and-down motion within the fluid.

8. The system according to claim 1, wherein the stirring/agitation mechanism further includes,
- a spacer located within an interior area of the pipette;
- a first internal magnet positioned on a first surface of the spacer;
- a second internal magnet positioned on a second surface of the spacer, the second internal magnet connected to the fiber or rod;
- an actuation point provided by an actuation magnet located at a first position in operative association with one of the first internal magnet or second external magnet, wherein movement of the actuation magnet causes movement of the first and second internal magnets, which in turn move the fiber or rod.

9. The system according to claim 1, wherein the stirring/agitation mechanism further includes a suspension component attached to an interior section of the pipette tip, and from which the fiber or rod extends.

10. The system according to claim 1, wherein the stirring/agitation mechanism further includes a fiber/rod suspension component and actuation point incorporated within the pipette tip.

11. The system according to claim 1, wherein the pipette tip is detachable from the pipette body portion.

12. A method for stirring/agitating fluid, comprising:
- inserting a pipette tip of a pipette into a fluid, wherein a fiber end or rod end of a fiber or rod of a stirring/agitation mechanism incorporated into the pipette extends through the pipette tip into the fluid; and
- activating the stirring/agitation mechanism causing the fiber end or rod end to move within the fluid and thereby stir or agitate the fluid.

13. The method according to claim 12, wherein the stirring/agitating of the fluid causes particles within the fluid which had adhered/settled to side walls or a bottom of a container in which the fluid is held to motivate at least some of the adhered/settled particles to become suspended within the fluid.

14. The method according to claim 13, further comprising, extracting the fluid from the container.

15. The method according to claim 14, wherein the stirring/agitation mechanism is active during the extracting step.

16. The method according to claim 14, wherein the stirring/agitation mechanism is stopped prior to the extracting step.

17. The method of claim 12, wherein the fluid is comprised of at least two different fluids and the stirring/agitating acts to mix the at least two different fluids together.

18. The method according to claim 17, wherein one of the fluids is within the pipette prior to the step of activating the stirring/agitation mechanism, and is expelled from the pipette into the container prior to, during or after the step of activating the stirring/agitation mechanism, wherein the step of activating the stirring/agitation mechanism causes the at least two fluids to be mixed.

19. The method according to claim 12, further including driving vibration of the fiber or rod into a resonant mode with a vibration node in the vicinity of the pipette tip exit aperture.

20. The method according to claim 12, wherein the activating of the stirring/agitation mechanism further causes a second fiber end or rod end to move, and a narrowed exit aperture of the pipette tip acts like a fulcrum for movement of the fiber or rod end passing therethrough.

21. The method according to claim 12, wherein the activating step includes operating a generator to continuously sweep through a range of frequencies to find a resonant frequency for the fiber/rod.

* * * * *

UNITED STATES PATENT AND TRADEMARK OFFICE
CERTIFICATE OF CORRECTION

PATENT NO. : 7,448,287 B2
APPLICATION NO. : 11/537700
DATED : November 11, 2008
INVENTOR(S) : Jurgen H. Daniel and Meng H. Lean It is certified that error appears in the above-identified patent and that said Letters Patent is hereby corrected as shown below:

In the Specifications:

Replace the paragraph at Col. 1, lines 6-10, with the following paragraph:

This invention was made with Government Support under Contract No. W911NF-05-C-0075 awarded by the U.S. Army. The Government has certain rights in this invention.

Signed and Sealed this
Thirteenth Day of August, 2013

Teresa Stanek Rea
*Acting Director of the United States Patent and Trademark Office*